US009993657B2

(12) United States Patent
Schmidt (10) Patent No.: US 9,993,657 B2
(45) Date of Patent: *Jun. 12, 2018

(54) HEALTH APPLICATIONS FOR USING BIO-FEEDBACK TO CONTROL AN ELECTROMAGNETIC FIELD

(71) Applicant: Medical Energetics Ltd., Galway (IE)

(72) Inventor: David G. Schmidt, Poway, CA (US)

(73) Assignee: MEDICAL ENERGETICS LTD., Galway (IE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/361,955

(22) Filed: Nov. 28, 2016

(65) Prior Publication Data

US 2017/0072213 A1    Mar. 16, 2017

Related U.S. Application Data

(63) Continuation of application No. 14/194,412, filed on Feb. 28, 2014, now Pat. No. 9,504,844.

(60) Provisional application No. 61/956,629, filed on Jun. 12, 2013.

(51) Int. Cl.
| | | |
|---|---|---|
| *A61N 2/02* | (2006.01) | |
| *A61N 2/00* | (2006.01) | |
| *A61N 1/40* | (2006.01) | |
| *H01F 5/00* | (2006.01) | |
| *H01F 5/02* | (2006.01) | |
| *H01F 5/04* | (2006.01) | |

(52) U.S. Cl.
CPC ............... *A61N 2/02* (2013.01); *A61N 1/40* (2013.01); *A61N 2/002* (2013.01); *A61N 2/006* (2013.01); *A61N 2/008* (2013.01); *H01F 5/00* (2013.01); *H01F 5/02* (2013.01); *H01F 5/04* (2013.01)

(58) Field of Classification Search
CPC ................................................ A61N 2/00–2/12
See application file for complete search history.

(56) References Cited

U.S. PATENT DOCUMENTS

| | | |
|---|---|---|
| 1,898,661 A | 2/1933 | Hagen |
| 2,035,274 A | 3/1936 | Mougey |
| 3,066,295 A | 11/1962 | Krause |
| 3,760,812 A | 9/1973 | Timm |
| 3,774,452 A | 11/1973 | Tullos |
| 4,266,532 A | 5/1981 | Ryaby |
| 4,439,702 A | 3/1984 | Belikov |
| 4,489,276 A | 12/1984 | Yu |
| 4,832,051 A | 5/1989 | Jarvik |
| 5,077,934 A | 1/1992 | Liboff |
| 5,079,458 A | 1/1992 | Schuster |
| 5,173,669 A | 12/1992 | Manoly |

(Continued)

FOREIGN PATENT DOCUMENTS

| | | |
|---|---|---|
| GB | 479841 A | 2/1938 |
| GB | 2480610 A | 11/2011 |

(Continued)

*Primary Examiner* — Thaddeus Cox
(74) *Attorney, Agent, or Firm* — ARC IP Law, PC; Joseph J. Mayo (57) ABSTRACT

An electrical system controlled, driven by and/or based on naturally occurring electrophysiological signals in a patient's body is used to produce useful electromagnetic fields for health applications and/or medical applications provided to the patient.

8 Claims, 3 Drawing Sheets

(56) References Cited

U.S. PATENT DOCUMENTS

| | | |
|---|---|---|
| 5,182,537 A | 1/1993 | Thuis |
| 5,339,061 A | 8/1994 | Reick |
| 5,359,340 A | 10/1994 | Yokota |
| 5,366,493 A | 11/1994 | Scheiner |
| 5,464,456 A | 11/1995 | Kertz |
| 5,654,723 A | 8/1997 | Craven |
| 5,819,467 A | 10/1998 | Zucker |
| 5,892,480 A | 4/1999 | Killen |
| 5,909,165 A | 6/1999 | Leupold |
| 5,954,630 A | 9/1999 | Masaki |
| 5,977,932 A | 11/1999 | Robinson |
| 6,005,462 A | 12/1999 | Myers |
| 6,169,523 B1 | 1/2001 | Ploussios |
| 6,239,760 B1 | 5/2001 | VanVoorhies |
| 6,300,920 B1 | 10/2001 | Pertl |
| 6,552,530 B1 | 4/2003 | Vaiser |
| 6,770,023 B2 | 8/2004 | Vaiser |
| 6,921,042 B1 | 7/2005 | Goodzeit |
| 6,978,179 B1 | 12/2005 | Flagg |
| 7,148,783 B2 | 12/2006 | Parsche |
| 7,154,368 B2 | 12/2006 | Sweeney |
| 7,375,449 B2 | 5/2008 | Butterfield |
| 8,463,407 B2 | 6/2013 | Bulkes |
| 8,652,023 B2 | 2/2014 | Schmidt |
| 8,653,925 B2 | 2/2014 | Schmidt |
| 8,749,333 B2 | 6/2014 | Schmidt |
| 8,919,035 B2 | 12/2014 | Schmidt |
| 8,961,384 B2 | 2/2015 | Schmidt |
| 9,030,283 B2 | 5/2015 | Schmidt |
| 2003/0169132 A1 | 9/2003 | Vaiser |
| 2005/0121396 A1 | 6/2005 | Kosakewich |
| 2008/0161884 A1 | 7/2008 | Chandler |
| 2008/0266203 A1 | 10/2008 | Rossetto |
| 2009/0206974 A1 | 8/2009 | Meinke |
| 2009/0260849 A1 | 10/2009 | Cardas |
| 2010/0005711 A1 | 1/2010 | McNeff |
| 2010/0057655 A1 | 3/2010 | Jacobson |
| 2010/0113862 A1 | 5/2010 | Kotowich |
| 2010/0152811 A1 | 6/2010 | Flaherty |
| 2010/0179630 A1 | 7/2010 | Williams |
| 2012/0101366 A1 | 4/2012 | Ruohonen |
| 2012/0143285 A1 | 6/2012 | Wang |
| 2012/0223800 A1 | 9/2012 | Schmidt |
| 2013/0192129 A1 | 8/2013 | Schmidt |
| 2013/0211181 A1 | 8/2013 | Schmidt |
| 2013/0261484 A1* | 10/2013 | Schmidt ............... A61B 7/04 600/528 |
| 2013/0285782 A1 | 10/2013 | Schmidt |
| 2014/0097925 A1 | 4/2014 | Schmidt |
| 2014/0100412 A1 | 4/2014 | Schmidt |
| 2014/0218149 A1 | 8/2014 | Schmidt |
| 2014/0371514 A1 | 12/2014 | Schmidt |
| 2015/0119630 A1 | 4/2015 | Schmidt |
| 2015/0119631 A1 | 4/2015 | Schmidt |
| 2015/0119632 A1 | 4/2015 | Schmidt |
| 2015/0157871 A1 | 6/2015 | Schmidt |
| 2015/0283393 A1 | 10/2015 | Schmidt |
| 2015/0283394 A1 | 10/2015 | Schmidt |

FOREIGN PATENT DOCUMENTS

| | | |
|---|---|---|
| WO | 2012118971 A2 | 9/2012 |
| WO | 2013112810 A1 | 8/2013 |
| WO | 2013123009 A1 | 8/2013 |

* cited by examiner

HEALTH APPLICATIONS FOR USING BIO-FEEDBACK TO CONTROL AN ELECTROMAGNETIC FIELD

FIELD OF THE INVENTION

The invention relates to electrical devices and/or systems configured to provide therapy to patients by using electromagnetic fields, and, in particular, devices and systems in which the generated electromagnetic field for a patient dynamically corresponds to measurements of electrophysiological information related to one or more organs or body parts of the patient.

BACKGROUND OF THE INVENTION

It is known that spirally wound electrical conductors exhibit certain electromagnetic properties and/or can be used to generate particular electromagnetic fields. For example, it is known that an electromagnetic coil may act as an inductor and/or part of a transformer, and has many established useful applications in electrical circuits. Applications of an electromagnetic coil may exploit the electromagnetic field that is created when, e.g., an active current source is operatively coupled to the coil.

SUMMARY

One aspect of the invention relates to a system for providing therapy to a subject and/or promoting health effects in a subject. The system may include one or more of a field generator, one or more sensors, one or more current sources, a transducer, and/or other components. The field generator may have electrical leads. The field generator may be configured to generate an electromagnetic field in response to an electric current being induced across the electrical leads. The one or more sensors may be configured to generate output signals conveying electrophysiological information. The one or more sensors may be configured to generate output signals pertaining to measurements of electrophysiological information of the subject. Electrophysiological information may include information related to one or more organs or body parts of the subject, including but not limited to heart, brain, kidney, liver, pancreas, spine, various cells of the body, and/or other organs or body parts of the subject. As used herein, the term "body parts" includes any organs of the subject, any cells of the subject, as well as any other parts of the body of the subject. The one or more current sources may be configured to induce one or more currents across electrical leads, including but not limited to the electrical leads of the field generator. In some embodiments, the one or more currents may include an alternating current. In some embodiments, one or more induced currents may correspond to one or more sensor-generated output signals. The transducer may be configured to convert acoustic signals to electrical signals and/or vice versa. In some embodiments, the one or more induced currents may correspond to one or more signals generated by the transducer.

In some embodiments, the field generator may include one or more of a support structure, one or more conductive wires, and/or other components. In some embodiments, the support structure may include two intertwined helically wound runners arranged in at least two complete revolutions per runner, referred to as a first runner and a second runner. The support structure may be arranged in a toroidal shape having a centroid. The centroid may be arranged at or near one or both of a subject and/or a body part of the subject, e.g. during therapy.

A conductive wire may be wound spirally around the first runner and/or the second runner. In some embodiments, a conductive wire may be wound spirally around each runner, e.g. in embodiments that include a first wire and a second wire. In some embodiments, multiple conductive wires may be wound spirally around individual runners. The leads of one or more conductive wires may be configured to be electrically coupled with one or more current sources to receive one or more currents through the conductive wires such that an electromagnetic field is created at or near the centroid that provides therapy to the subject.

As used herein, a "wire" may include a set of twisted wires (which may interchangeably be referred to as a "twisted wire"), including but not limited to a set of two twisted wires. The number of turns of a set of twisted wires per inch and/or per helical revolution of a runner may be characteristic measurements/features of the system. In some embodiments, the number of twists per inch of a twisted wire may be about 2, about 5, about 10, about 20, about 100, and/or another suitable number of twists. In some embodiments, the frequency characteristics of an alternating current and/or the corresponding generated electromagnetic field may be based on, proportional to, and/or otherwise related to the number of twists of a twisted wire. For example, a higher number of twists per inch may correspond to a higher operating frequency for the alternating current and/or the corresponding generated electromagnetic field. In some embodiments, multiple twisted wires (e.g. a first twisted wire wound around a first runner and a second twisted wire wound around a second runner) may have the same direction of twisting, and/or a different direction of twisting.

In some embodiments, a conductive wire may be spirally wound around the first runner to form a bifilar coil around the first runner. In some embodiments, another conductive wire may be spirally wound around the second runner to form a second bifilar coil around the second runner. In some embodiments, the two leads of the first wire are configured to be electrically coupled to a first current source to receive a first current. In some embodiments, the two leads of the second wire are configured to be electrically coupled to the same current source or to a different current source to receive a second current. The first current and/or second current generate an electromagnetic field. In some embodiments, the system may include one or more resistive elements. The one or more resistive elements may be coupled electrically to one or both of the first wire and/or the second wire such that a nominal impedance of the first wire, the second wire, and the one or more resistive elements has a predetermined value that substantially matches an impedance of one or more current sources.

In some embodiments, the system may include one or more processors configured to execute computer program modules. The one or more processors may include physical processors. The computer program modules may include one or more of an input module, a processing module, a playback module, and/or other computer program modules. The input module may be configured to obtain information based on sensor-generate output signals. The processing module may be configured to process the obtained information from the input module. In some embodiments, the processing module may be configured to generate a processed signal based on the obtained information form the input module. The playback module may be configured to produce sound signals based on one or more of the obtained information from the input module and/or the processed signal from the processing module. The sound signals produced by the playback module may be coupled electrically to the leads of the one or more conductive wires such that the induced current corresponds to and/or is based on the sound signals. In some embodiments, one or more frequencies of the induced (alternating) current may correspond to one or more frequencies of either the sensor-generated output signals and/or the sound signals produced by the playback module.

One aspect of the invention relates to a method for providing therapy to a subject and/or promoting health effects in a subject. The method may include arranging a support structure at or near one or both of the subject and/or a body part of the subject, generating output signals conveying electrophysiological information of the subject, and inducing a current that generates an electromagnetic field at or near one or both of the subject and/or the body part of the subject. The support structure may include any of the features, functionality, and/or components as attributed to a support structure elsewhere within this disclosure. The induced current may correspond to and/or be based on sensor-generated output signals and/or information derived therefrom.

One aspect of the invention relates to a method for providing therapy to a subject and/or promoting health effects in a subject. The method may include arranging a support structure at or near one or both of the subject and/or a body part of the subject, generating output signals conveying electrophysiological information of the subject, converting the generated output signals to acoustic signals, and inducing a current that generates an electromagnetic field at or near one or both of the subject and/or the body part of the subject. The support structure may include any of the features, functionality, and/or components as attributed to a support structure elsewhere within this disclosure. The induced current may correspond to and/or be based on one or both of the sensor-generated output signals and/or the acoustic signals.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
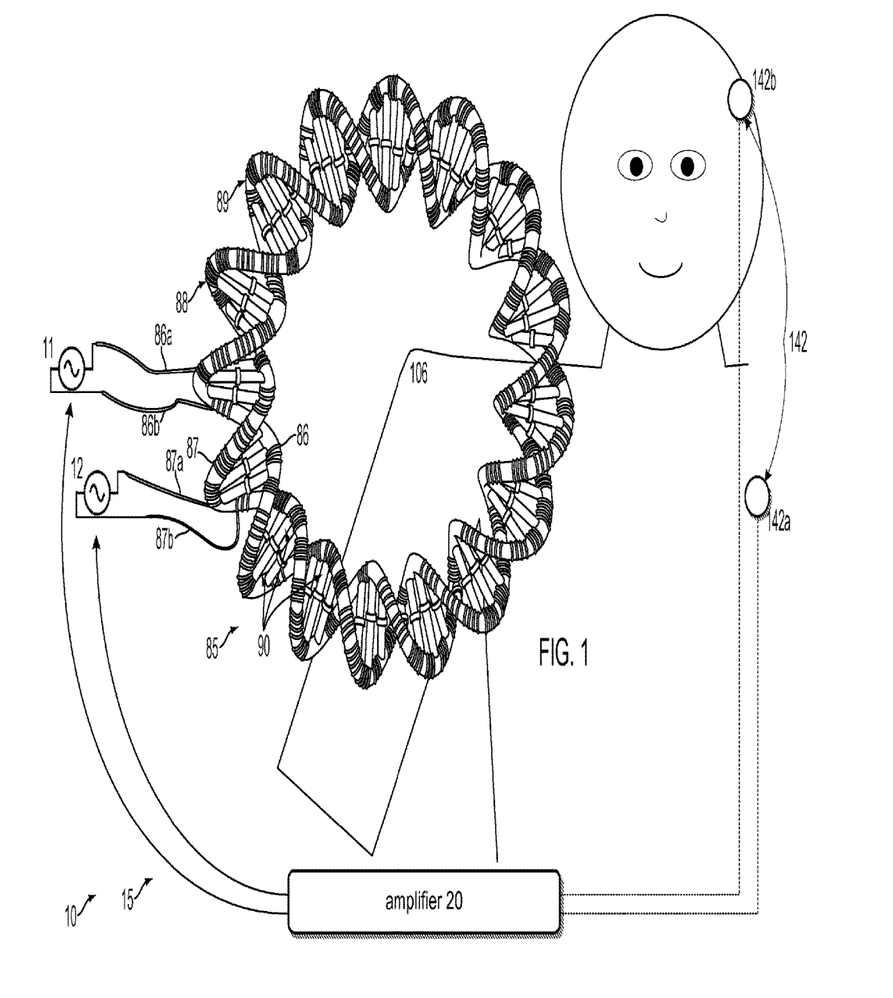
FIG. 1 schematically illustrates a system for providing therapy to a subject and/or promoting health effects in a subject, according to one or more embodiments.

FIG. 1 illustrates a system 10 for providing therapy to a subject 106 and/or promoting health effects in subject 106, according to one or more embodiments. The therapy and/or health effects may include, but are not limited to, one or more of pain relief, pain management, relief of discomfort, reduction of inflammation, improved range of motion, hair growth, tissue repair, bone growth/repair, regenerative effects, improved circulation, improved micro-circulation, accelerated healing, rehabilitation, and/or other types of therapy and/or health effects on living organisms. The therapy and/or health effects may be used for various medical conditions, including but not limited to diabetic neuropathy, and/or other neuropathic disorders. The therapy and/or health effects may be used in conjunction with various medical treatments, techniques, and/or technologies, including but not limited to stem cell therapy, regenerative medicine, rehabilitation, and/or other types of therapy.

Figure 2:
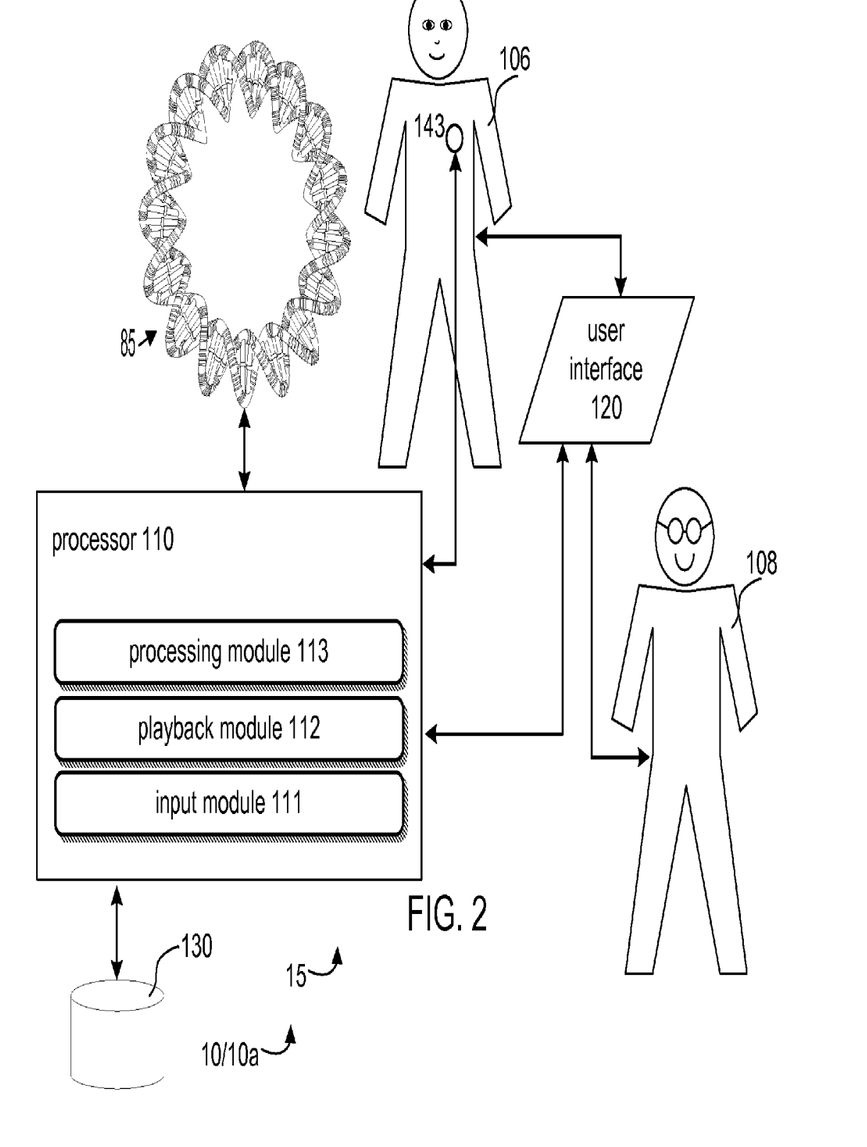
FIG. 2 schematically illustrates a system for providing therapy to a subject and/or promoting health effects in a subject, according to one or more embodiments.

System 10 may operate on organs, tendons, ligaments, bones, spine, and/or other parts of a body. System 10 may be placed anywhere on the body of subject 106. System 10 may include one or more of a field generator 15, one or more sensors 142, one or more current sources (e.g. including a current source 11 and/or a current source 12), an amplifier 20, and/or other components. Referring to FIG. 2, in some embodiments, system 10 may include one or more of a transducer 143, one or more processors 110, a user interface 120, electronic storage 130, an input module 111, a playback module 112, a processing module 113, and/or other components and/or modules. Features depicted in the figures and described in this disclosure may be combined in some embodiments.

Referring to FIG. 1, in some embodiments, field generator 15 may include one or more of a support structure 85, a first wire 86, and/or other wires and/or components. The depiction of the size of subject 106 relative to the size of support structure 85 is not meant to be limiting.

Support structure 85 of system 10 in FIG. 1 as depicted includes two intertwined helically wound runners—runner 88 and runner 89—sharing the same (circular) axis, coupled by struts 90 and having one or more conductive wires spirally wound around one or both runners. In other words, runner 88 and runner 89 of support structure 85 form cores around which wire 86 and wire 87 are spirally wound, respectively. As depicted in FIG. 1, support structure 85 includes two wires: wire 86 and wire 87. In some embodiments, system 10 may include one runner, three runners, and/or another number of runners.

Runner 88 and runner 89 of support structure 85 and system 10 in FIG. 1 are arranged in the shape of a three-dimensional curve similar to or substantially the same as a helix, bend, twisted, and/or shaped with its ends arranged together. It is noted that the shape of support structure 85 resembles the general shape of DNA. The pitch of a helix may be the width of one 360 degree helix turn (a.k.a. revolution), e.g. measured parallel to the axis of the helix. Intertwined helically wound runners may share the same axis, be congruent, and/or differ by a translation along the axis, e.g. measuring half the pitch. The pitch of the helical shape of the runners in field generator 15 may range from about ¼ inch, about ½ inch, about an inch, about 2 inches, about 3 inches, about 6 inches, about a foot, and/or other suitable pitches.

The two runners shown in FIG. 1 may share the same axis, extending for approximately eight complete revolutions, as an exemplary embodiment. In some embodiments, the number of revolutions may be any number between 2 and about 100, and/or another suitable number. A helical shape may have constant pitch, constant radius (measured in the plane perpendicular to the axis), constant torsion, constant curvature, constant ratio of curvature to torsion, and/or a straight axis. As depicted in FIG. 1, the helical shape formed by the runners may have a circular axis, and the field generator may thus have a toroidal shape. The measure of how tightly wound the runners in a field generator are may be characterized by one or more other measures, and/or combinations/ratios of measures, including but not limited to the pitch of the runners, the pitch of the wound wire, the radius of the helical shape (e.g. the radius of the cross-sectional area of the toroidal shape, perpendicular to the plane in which the runners form a circle), the angle formed by the runners (e.g. the angle, between 0 and 90 degrees, of a runner with the cross-sectional plane of its helix, such that a zero angle corresponds to a zero pitch, and a 90 degree angle corresponds to an infinite pitch), the distance between revolutions, and/or other characteristic measures or combinations thereof.

The shape of the cross-section of a runner may include one or more of a circle, an oval, a square, a triangle, a rectangle, an angular shape, a polygon, and/or other shapes. The width and height of the cross-section of a runner may be limited for practical purposes. For example, for the purposes described herein, in some embodiments, it may be preferred to arrange support structure 85 such that there is available space within the periphery of support structure 85, as shown, e.g., in FIG. 1. As depicted in FIG. 1, the shape of the cross-section of runner 88 and runner 89 may be a circle. Note that embodiments of this disclosure are not intended to be limited by any of the given examples.

Runner 88, runner 89 and/or struts 90 of system 10 in FIG. 1 may be manufactured from one or more of plastic, plastic plated with metals including copper, nickel, iron, soft iron, nickel alloys, and/or other metals and alloys, and/or other materials. In some embodiments, individual runners may be made from magnetic material. In some embodiments, individual runners may be made from and/or include magnetically permeable material. Alternatively, and/or simultaneously, in some embodiments, individual runners may be made from and/or include non-ferromagnetic material. In some embodiments, multiple runners within the same system may be made from different materials. In some embodiments, runner 88, runner 89 and struts 90 are manufactured from non-conductive material. Runner 88, runner 89, and struts 90 may be manufactured from different materials. Runner 88, runner 89, and struts 90 may be manufactured through integral construction or formed separately prior to being assembled. The preceding statement is not intended to limit the (process of) manufacture of bodies similar to or substantially the same as support structure 85 in any way.

Referring to FIG. 1, wire 86 and wire 87, as any wire listed in any figure included in this description, may be insulated, uninsulated, or partially insulated and partially uninsulated.

The shape of support structure 85 of system 10 in FIG. 1 may be generally toroidal. In some embodiments, the support structure of system 10 may be arranged in any planar shape, including circular, polygonal, and/or other shapes. Alternatively, and/or simultaneously, a support structure such as support structure 85 may be arranged in a three-dimensional curve (a.k.a. space curve). Runner 88 and runner 89 of support structure 85 may form cores around which wire 86 and wire 87 are spirally wound, respectively. As such, wire 86 and wire 87 may be arranged in a helical shape having axes that coincide with runner 88 and runner 89, respectively. As shown in FIG. 1, wire 86 and 87 may be wound such that they go around any of struts 90 of support structure 85 and/or around any points of engagement between one of struts 90 and one of runners 88 and 89. The number of wire turns per complete revolution of a runner and/or the number of wire turns between adjacent struts may be characteristic measurements/features of support structure 85. In FIG. 1, wire 86 and wire 87 are arranged to make approximately three to five turns between adjacent struts associated with runner 88 and runner 89, respectively, and/or some other number of turns. The depiction of FIG. 1 is intended to be exemplary, and in no way limiting.

Wire 86 may include two leads—lead 86a and lead 86b. Wire 87 may include two leads—lead 87a and lead 87b. In system 10, support structure 85 is electrically coupled with one or more power sources and/or current sources, such as, e.g., current source 11 and/or current source 12, arranged such that electrical coupling with one or both of wire 86 and wire 87 may be established, e.g. through coupling of current source 11 with lead 86a and 86b of wire 86 and through coupling of current source 12 with lead 87a and 87b of wire 87. The current supplied to wire 86 may be a direct current or an alternating current. The current supplied to wire 87 may be a direct current or an alternating current. The currents supplied to wire 86 and wire 87 may flow in the same direction or the opposite direction. In some embodiments, the leads of wire 86 and wire 87 may be electrically coupled with the same current source.

For alternating currents, operating frequencies ranging from 0 Hz to 100 GHz are contemplated. Operating currents ranging from 1 pA to 10 A are contemplated. Operating voltages ranging from 1 mV to 20 kV are contemplated. In some embodiments, a root mean square voltage of less than about 1.6 V is supplied to wire 86 and/or wire 87. In some embodiments, a root mean square voltage of greater than about 0.25 V is supplied to wire 86 and/or wire 87. In a preferred embodiment, the frequency of the alternating current supplied to wire 86 and/or wire 87 is between 0 Hz and 20 kHz, or in the audible range. In some embodiments, the current is less than about 1 pA, 1 nA, 1 mA, 100 mA, 250 mA, 500 mA, and/or other amounts of current. The operating frequencies for wire 86 and wire 87 may be the same or different. Other electrical operating characteristics of current supplied to wire 86 and wire 87, such as phase, may be the same or different. System 10 may be used to exploit the electromagnetic field that is created in and/or around support structure 85 when electrical power is supplied to one or more wires of support structure 85. The electromagnetic field provides therapy to subject 106 and/or promotes health effects in a subject.

For the purposes of this description, the electromagnetic field may be an electromagnetic field of at least a predetermined threshold level of tesla. The predetermined threshold may be 1 pT, 1 nT, 1 mT, 10 mT, 100 mT, and/or another threshold. In some embodiments, the electromagnetic field may have a strength ranging between about 0.1 milligauss and about 100 milligauss, between about 1 milligauss and about 500 milligauss, and/or other ranges. The strength of the electromagnetic field may be measured at a predetermined distance from field generator 15 and/or support structure 85. The predetermined distance for such measurements may be about 1 inch, about 1 foot, about 3 feet, about 6 feet, and/or another distance.

Some embodiments of an electrical system including a support structure similar to or substantially the same as support structure 85 in FIG. 1, thus including wire 86 and wire 87, may be configured to have a current in wire 86 flowing in the opposite direction as the current flowing in wire 87. In some embodiments the current supplied to one wire may be a direct current, whereas the current supplied to another wire may be an alternating current. By way of non-limiting example, additional structures for a support structure and/or electrical systems using a support structure (referred to as "body") may be described in U.S. patent application Ser. No. 13/457,347, filed Apr. 26, 2012, and titled "System Configuration Using A Double Helix Conductor," as well as U.S. patent application Ser. No. 13/213,604, entitled "Double Helix Conductor," and filed Aug. 19, 2011, which are hereby incorporated into this disclosure by reference in its entirety. These patent applications may also be referred to as "the '347 application" and "the '604 application" herein. By way of non-limiting example, additional health applications, as well as structures for a support structure and/or electrical systems using a support structure (referred to as "body") may be described in U.S. patent application Ser. No. 13/458,716, filed Apr. 27, 2012, and titled "Health Applications of a Double Helix Conductor," which is hereby incorporated into this disclosure by reference in its entirety. This patent application may also be referred to as "the '716 application" herein.

Some embodiments of an electrical system including a support structure similar to or substantially the same as support structure 85 may be configured to include one or more conductive wires that are wound to form a bifilar coil around one or more runners. In some embodiments, the windings may be one or more of caduceus windings, Ayrton-Perry winding, trifilar windings, windings of braided wires, windings of twisted wires, and/or other types of windings. By way of non-limiting example, additional windings may be described in the '347 application and additional details of a support structure (referred to as "body") may be described in the '604 application.

In some embodiments, system 10 may include multiple support structures similar to or substantially the same as support structure 85. Currents for these multiple support structures may be supplied by one or more power sources and/or current sources.

In some embodiments, support structure 85 may be configured such that the dimensions of the available space within the periphery of support structure 85 and/or the passage formed through the centroid of the shape of support structure 85 are predetermined dimensions. In some embodiments, a predetermined dimension may include a diameter of about 1 inch, about 1 foot, about 2 feet, about 4 feet, about 6 feet, and/or another suitable dimension. Suitable dimensions may depend on average sizes of human fingers, wrists, elbows, arms, ankles, knees, legs, shoulders, (lower) backs, torsos, bodies, and/or other body parts, as may be used as an area to receive treatment and/or therapy. By way of non-limiting example, additional information regarding (full-body) applications of electrical system similar to the systems described herein may be described in the '716 application.

In some embodiments, lead 86*a* and 86*b* of wire 86 and lead 87*a* and 87*b* of wire 87 are electrically coupled in the same circuit. This circuit may include, for example, one or more resistive components, such as resistors, that are arranged such that the circuit has a nominal impedance of a predetermined value, such as, e.g., 4 ohms, 8 ohms, 16 ohms, 32 ohms, 100 ohms, 600 ohms, and/or another predetermined value. In some embodiments, the predetermined value may be chosen to match the impedance of standard consumer electronics components and/or systems, including for example audio consumer electronics. These examples are not intended to be limiting in any way. By way of non-limiting example, additional information regarding resistive elements and/or impedance matching may be described in the '347 application.

Referring to FIG. 1, the one or more sensors 142 are configured to generate output signals conveying electrophysiological information and/or measurements related to one or more organs and/or body parts of subject 106. The one or more sensors 142 may be placed anywhere on the body of subject 106. In some embodiments, the one or more sensors 142 may be non-invasive. For example, the one or more sensors 142 may be configured to not penetrate the skin of subject 106, but rather to be placed against or near the skin of subject 106. The one or more sensors 142 may include, as depicted in FIG. 1, a (first) sensor 142*a* and a (second) sensor 142*b*. The placement, type, and number of sensors 142 is not intended to be limited by the depictions in any figures. In some embodiments, system 10 may include 1 sensor, 3 sensors, and/or another number of sensors. As depicted in FIG. 1, sensor 142*a* may be positioned at or near the heart of subject 106 (e.g. on the skin of the chest of subject 106). As depicted in FIG. 1, sensor 142*b* may be positioned and/or located at or near the brain of subject 106 (e.g. on or near the head or skull of subject 106).

In some embodiments, the one or more sensors 142 may include an audio sensor, a microphone, a stethoscope, an electronic stethoscope, a pressure sensor, a motion sensor, a proximity sensor, an electromagnetic sensor, an electrode, a temperature sensor, a current sensor, an optical sensor, an electro-optical sensor, a heart monitor, an electro interstitial scanning (EIS) sensor and/or device, a bioelectrical impedance sensor and/or device, a BioPulsar©, and/or other sensors, devices, and/or combinations thereof. In some embodiments, the one or more sensors 142 may be configured to measure electrical and/or electrophysiological signals at or near subject 106, and/or emitted by subject 106. The one or more sensors 142 may be configured to convey sounds, currents, voltages, electromagnetic fields caused and/or emitted naturally by subject 106. Measured signals may pertain to respiratory characteristics and/or parameters of subject 106, cardiac/coronary characteristics and/or parameters of subject 106, hemodynamic characteristics and/or parameters of subject 106, neural characteristics and/or parameters of subject 106, brain-related characteristics and/or parameters of subject 106, and/or other characteristics and/or parameters. In some embodiments, measured signals may pertain and/or correspond to electroencephalography (EEG) measurements, magneto-encephalography (MEG) measurements, electrocardiography (EKG or ECG) measurements, heart rate variability (HRV) measurements, acoustic cardiograph (ACG) measurements, and/or other measurements, in particular measurements of bioelectrical signals generated by the human body. As used herein, correspondence of a generated output signal to, for example, an EEG signal refers to a generated output signal that includes similar information as a sensor-generated signal used for a standard EEG measurement. In some embodiments, measurements may be related to heart function, for example pertaining to the P wave, the PR interval, the PR segment, the QRS complex, the ST segment, the T wave, the ST interval, the QT interval, the U wave, the J wave, one or more heart valves, and/or other functions/periods/amplitudes that may be measured using EKG, derivatives thereof, and/or combinations thereof. Alternatively, and/or simultaneously, measurements related to heart functions may pertain to levels, functions, periods, and/or amplitudes that may be measured by techniques other than EKG.

In some embodiments, the one or more sensors 142 may be configured to generate output signals in an ongoing manner, e.g. throughout the day or during a treatment session. This may include generating signals intermittently, periodically (e.g. at a sampling rate), continuously, continually, at varying intervals, and/or in other ways that are ongoing during at least a portion of period of a day, week, month, treatment, or other duration. The sampling rate may be about 0.001 second, 0.01 second, 0.1 second, 1 second, about 10 seconds, about 1 minute, and/or other sampling rates. It is noted that multiple individual sensors may operate using different sampling rates, as appropriate for the particular output signals and/or (frequencies related to particular) parameters derived therefrom. For example, in some embodiments, the generated output signals may be considered as a vector of output signals, such that a vector includes multiple samples of information conveyed related to one or more types of electrophysiological information of subject 106. Different parameters may be related to different vectors. A particular parameter determined in an ongoing manner from a vector of output signals may be considered as a vector of that particular parameter.

Referring to FIG. 1, in some embodiments, system 10 may include amplifier 20. Amplifier 20 may be configured to amplify signals. Amplifier 20 may include one or more inputs and one or more outputs, such that amplifier 20 amplifies the signal presented on the one or more inputs and provides the amplified signal to the one or more outputs. Amplifier 20 may include and/or support multiple channels. The input signals for amplifier 20 may be electrically coupled to and/or based on sensor-generated output signals from the one or more sensors 142. In some embodiments, the sensor-generated output signal may include an acoustic and/or audible signal. The output signals of amplifier 20 may be electrically coupled to and/or form the basis of the signals driving field generator 85. In some embodiments, output signals from amplifier 20 may be directly electrically coupled to the electrical leads of wire 86 and/or wire 87 without use of current source 11 or current source 12. In some embodiments, output signals from amplifier 20 may be used to control the operation of current source 11 and/or current source 12, which in turn may induce one or more electrical currents through wire 86 and/or wire 87. In some embodiments, the one or more induced alternating currents may be dynamically controlled such that one or more frequencies of one or more alternating currents correspond to one or more frequencies of the sensor-generated output signals.

In some embodiments, a first channel of amplifier 20 may be operatively connected to first runner 88 of system 10 such that a current flows in a first particular direction. Simultaneously, a second channel of amplifier 20 may be operatively connected to second runner 89 of system 10 such that a current flows in a second particular direction. In some embodiments, system 10 may be configured such that the first particular direction is opposite from the second particular direction.

By way of illustration, FIG. 2 schematically illustrates a system 10a for providing therapy to a subject and/or promoting health effects in a subject. System 10a may include similar or the same features as system 10 in FIG. 1. For example, support structure 85 of system 10a in FIG. 2 may be similar to or the same as support structure 85 of system 10 in FIG. 1, and so forth.

System 10a may include, in addition to any of the components, features, and functionality described in relation to system 10 (FIG. 1), one or more of processor(s) 110, user interface 120, electronic storage 130, transducer 143, one or more computer program modules, and/or other components.

Transducer 143 may include one or more of a microphone, a stethoscope (analog and/or digital), and/or other devices and/or components. Transducer 143 may be configured to convert acoustic signals to one or more electrical signals.

Processor 110 of system 10a in FIG. 2 is configured to provide information processing capabilities in system 10a. As such, processor 110 includes one or more of a digital processor, an analog processor, a digital circuit designed to process information, a central processing unit, a graphics processing unit, an analog circuit designed to process information, and/or other mechanisms for electronically processing information. Although processor 110 is shown in FIG. 2 as a single entity, this is for illustrative purposes only. In some embodiments, processor 110 may include a plurality of processing units.

As is shown in FIG. 2, processor 110 is configured to execute one or more computer program modules. The one or more computer program modules may include one or more of input module 111, playback module 112, processing module 113, and/or other modules. Processor 110 may be configured to execute modules 111-113 by software; hardware; firmware; some combination of software, hardware, and/or firmware; and/or other mechanisms for configuring processing capabilities on processor 110.

It should be appreciated that although modules 111-113 are illustrated in FIG. 2 as being co-located within a single processing unit, in embodiments in which processor 110 includes multiple processing units, one or more of modules 111-113 may be located remotely from the other modules. The description of the functionality provided by the different modules 111-113 described herein is for illustrative purposes, and is not intended to be limiting, as any of modules 111-113 may provide more or less functionality than is described. For example, one or more of modules 111-113 may be eliminated, and some or all of its functionality may be incorporated, shared, integrated into, and/or otherwise provided by other ones of modules 111-113. Note that processor 110 may be configured to execute one or more additional modules that may perform some or all of the functionality attributed below to one of modules 111-113.

Input module 111 may be configured to obtain information. In some embodiments, the information may be obtained based on sensor-generated output signals. In some embodiments, the information may be obtained based on an electrical signal from transducer 143. In some embodiments, the information may be obtained through a microphone or other acoustic-to-electric transducer and/or sensor. For example, input module 111 may be configured to obtain an electrical signal that represents the sound of the heartbeat of subject 106, and/or one or more sounds related to the mitral valve, the tricuspid valve, the aortic valve, and/or the pulmonary valve of subject 106.

In some embodiments, the information may be obtained from storage, e.g. from electronic storage. Information obtained from storage may include electronic audio files (also referred to as audio tracks) in any format, including but not limited to MP3, WMA, WAV, AIFF, and/or other audio formats. Audio formats may be uncompressed, have lossless compression, and/or lossy compression. In some embodiments, the obtained information may include an audio track of one or more people saying, singing, and/or chanting. For example, the one or more people may generate and/or produce the traditional "OM" sound (e.g. as known in Hinduism).

In some embodiments, information may be obtained from traditional sound sources including phonographs, CD-players, DVD players, AM radio, FM radio, and/or other sound sources. Electronic storage may be local to system 10a and/or be accessible from a remote location through a network connection, such as e.g. the internet. In some embodiments, information obtained by input module 11 may be a combination of one or more of sensor-generated output signals (from one or more sensors 142), one or more electrical signals (from transducer 143), and/or information obtained from storage.

Processing module 113 may be configured to process the obtained information from input module 111. Processing module 113 may be configured to generate a processed signal based on the obtained information. For example, processing module 113 may convert, filter, modify, and/or otherwise transform information or signals from input module 111 to generate the processed signal. In some embodiments, the obtained signal may be a coronary or cardiac signal having a first range of frequencies. Processing module 113 may be configured to transform the first range of frequencies into a second range of frequencies, using signal processing techniques, such that the second range of frequencies may be suitable for acoustic reproduction of the processed signal. In some embodiments, the obtained signal may represent brain activity, and have a first range of frequencies. Through filtering, conversion, transformation, and/or other signal processing techniques, the processed signal may have a second range of frequencies. The second range may be suitable for acoustic reproduction.

Playback module 112 may be configured to produce sound signals based on the processing signal from processing module 112. In some embodiments, playback module 112 may be configured to produce sound signals based on the obtained information from input module 111. For example, playback module 112 may be configured to produce sound signals based on the obtained electrical signal that represents the sound of the heartbeat of subject 106. The produced sound signals, though possibly processed through processing module 112, may represent the sound of the heartbeat of subject 106. Other naturally occurring sounds or electromagnetic signals produced or emitted by subject 106 are considered within the scope of this disclosure.

The sound signals produced by playback module 112 may be analog and/or digital signals. The sound signals produced by playback module 112 may be electric, optical, and/or using other media. The sound signals produced by playback module 112 may be accessible through one or more signal connectors, including but not limiting to line out connectors, tip-ring-sleeve (TRS) connectors, tip-ring-ring-sleeve (TRRS) connectors, TOSLINK connectors, S/PDIF connectors, FireWire™ connectors, HDMI connectors, DVI connectors, USB connectors, and/or other connectors capable of transferring an audio signal. The sound signals produced by playback module 112 may be electrically coupled to the leads of the one or more conductive wires of support structure 85 (depicted in FIG. 2) such that current through the one or more conductive wires of support structure 85 corresponds to the produced sound signals.

In some embodiments, the sound signals produced by playback module 112 may be amplified by amplifier 20 before being electrically coupled to the leads of the one or more conductive wires of support structure 85. In some preferred embodiments, amplifier 20 may be an audio amplifier ranging between 100 W and 400 W. Other types of amplifiers and/or amplifiers having a different power range are also contemplated.

In some embodiments, the sound signals produced by playback module 112 may be used to control one or more current sources, e.g. current source 11 and/or current source 12, which in turn induce alternating currents in field generator 15 as described elsewhere.

In some embodiments, system 10 may be configured such that the cross-section of the toroidal shape of field generator 15 is between about 3 inches and about 8 inches, and such that the diameter of the passage formed through support structure 85 is between about 1 foot and about 4 foot. In some embodiments, field generator 15 may be suspended between about 1 foot and about 3 foot from (e.g. above) subject 106 and/or, in particular, from the body part of subject 106 that is to be treated. For example, to treat lower back pain, field generator 15 may be suspended about 1 foot above the painful area. By way of example, and not limitation, a treatment may include multiple periods during which amplifier 20 is set to different percentages of output power. For example, during the first period of 5 minutes, amplifier 20 may be set to 25% of available power, during the second period of 5 minutes, amplifier 20 may be set to 50% of available power, during the third period of 5 minutes, amplifier 20 may be set to 75% of available power, and during the fourth period of between 5 and 15 minutes, amplifier 20 may be set to 100% of available power.

In some embodiments, system 10 may be configured to include transducer 143, e.g. an electronic microphone. Transducer 143 may be configured to produce acoustic cardiograph (ACG) signals, e.g. by connecting an ACG to the electronic microphone. The ACG signal may be amplified by amplifier 20. One or two channels of amplifier 20 may be operatively connected to one or both runners (i.e. to the coils formed on the runners) of field generator 15. For example, two channels may be operatively connected such that the currents through the coils flow in opposite directions. Transducer 143 may be arranged near subject 106 such that transducer 143 picks up a signal representing electrophysiological information related to the heart of subject 106, e.g. the signal may be related to the aortic valve of subject 106. Field generator 15 may be suspended about 1 foot above the area of subject 106 that is to be treated. By way of example, and not limitation, a treatment may include multiple periods during which amplifier 20 is set to different percentages of output power. For example, during the first period of 5 minutes, amplifier 20 may be set to 25% of available power, during the second period of 5 minutes, amplifier 20 may be set to 50% of available power, during the third period of 5 minutes, amplifier 20 may be set to 75% of available power, and during the fourth period of between 5 and 15 minutes, amplifier 20 may be set to 100% of available power.

Electronic storage 130 of system 10a in FIG. 2 comprises electronic storage media that electronically stores information. The electronic storage media of electronic storage 130 may include one or both of system storage that is provided integrally (i.e., substantially non-removable) with system 10a and/or removable storage that is connectable to system 10a via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10a to function properly. For example, electronic storage 130 may store sound information and/or electronic audio files (as discussed elsewhere herein), and/or other information. Electronic storage 130 may be a separate component within system 10a, or electronic storage 130 may be provided integrally with one or more other components of system 10a (e.g., processor 110).

User interface 120 of system 10a in FIG. 2 is configured to provide an interface between system 10a and a user (e.g., user 108, subject 106, a caregiver, a therapy decision-maker, etc.) through which the user can provide information to and receive information from system 10a. This enables data, results, and/or instructions and any other communicable items, collectively referred to as "information," to be communicated between the user and system 10a. An example of information that may be conveyed to user 108 is an indication of the volume and/or intensity of the sound signals produced by playback module 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10a from removable storage (e.g., a smart card, a flash drive, a removable disk, etc.) that enables the user(s) to customize system 10a. Other exemplary input devices and techniques adapted for use with system 10a as user interface 120 include, but are not limited to, an RS-232 port, RF link, an IR link, modem (telephone, cable, Ethernet, internet or other). In short, any technique for communicating information with system 10a is contemplated as user interface 120.

Figure 3A:
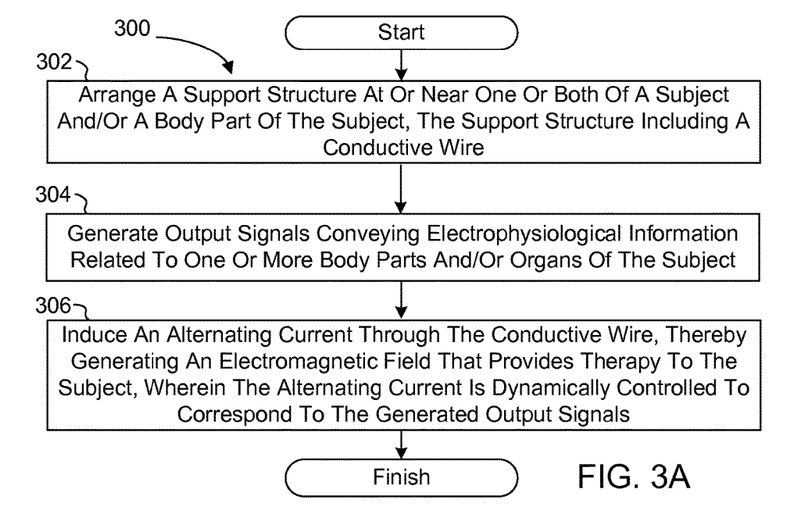
FIGS. 3A-3B illustrate methods for providing therapy to a subject and/or promoting health effects in a subject, according to one or more embodiments.
Figure 3B:
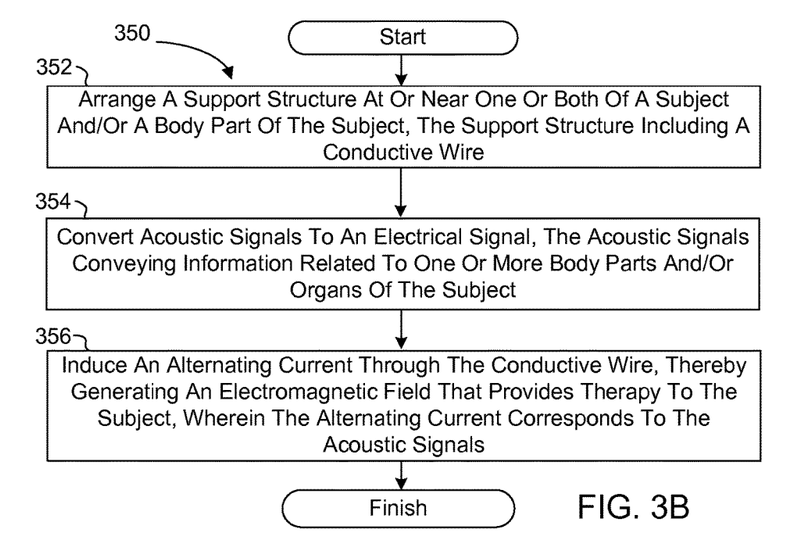

FIGS. 3A-3B illustrate methods 300-350 for providing therapy to a subject. The operations of methods 300-350 presented below are intended to be illustrative. In certain embodiments, methods 300-350 may be accomplished with one or more additional operations not described, and/or without one or more of the operations discussed. Additionally, the order in which the operations of methods 300-350 are illustrated in FIGS. 3A-3B and described below is not intended to be limiting.

In certain embodiments, methods 300-350 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of methods 300-350 in response to instructions stored electronically on an electronic storage medium. The one or more processing devices may include one or more devices configured through hardware, firmware, and/or software to be specifically designed for execution of one or more of the operations of methods 300-350.

Regarding method 300, at an operation 302, a support structure is arranged at or near one or both of a subject and/or a body part of the subject. The support structure includes a conductive wire. In one embodiment, operation 302 is performed by a user of system 10 (shown in FIG. 2 and described above).

At an operation 304, output signals are generated that convey electrophysiological information related to one or more organs of the subject. In one embodiment, operation 304 is performed by one or more sensors similar to or substantially the same as sensor(s) 142 (shown in FIG. 1 and described above).

At an operation 306, an alternating current is induced through the conductive wire, thereby generating an electromagnetic field that provides therapy to the subject. The alternating current is dynamically controlled to correspond to the generated output signals. In one embodiment, operation 306 is performed by one or more current sources similar to or substantially the same as current source 11 and/or current source 12 (shown in FIG. 1 and described above).

Regarding method 350, at an operation 352, a support structure is arranged at or near one or both of a subject and/or a body part of the subject. The support structure includes a conductive wire. In one embodiment, operation 352 is performed by a user of system 10 (shown in FIG. 2 and described above).

At an operation 354, acoustic signals are converted to an electrical signal. The acoustic signals convey information related to one or more organs of the subject. In one embodiment, operation 354 is performed by a transducer similar to or substantially the same as transducer 143 (shown in FIG. 2 and described above).

At an operation 356, an alternating current is induced through the conductive wire, thereby generating an electromagnetic field that provides therapy to the subject. The alternating current corresponds to the electrical signal. In one embodiment, operation 356 is performed by one or more current sources similar to or substantially the same as current source 11 and/or current source 12 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. For example, in some embodiments, system 10 may include amplifier 20 (shown in FIG. 1), as well as one or more computer program modules 111-113 (shown in FIG. 2).

What is claimed is:

1. A system for providing therapy to a subject by using electromagnetic fields, the system comprising:
   a field generator comprising electrical leads, wherein the field generator is configured to generate an electromagnetic field in response to an electric current being induced across the electrical leads;
   a transducer configured to convert acoustic signals conveying information related to one or more body parts of the subject to an electrical signal including frequencies that predominantly range between 20 Hz and 20 kHz;
   wherein an alternating current is induced across the electrical leads, wherein the induced alternating current is based on the electrical signal, and wherein one or more frequencies of the alternating current correspond to one or more frequencies of the electrical signal; and, one or more processors configured to execute computer program modules, the computer program modules comprising
- an input module configured to obtain information based on the electrical signal;
- a processing module configured to process the obtained information and generate a processed signal based on the obtained information; and,
- a playback module configured to produce sound signals based on the processed signal;
- wherein the induced alternating current is based on the produced sound signals.

2. The system of claim 1, wherein the field generator further comprises a support structure configured to be arranged at or near one or both of the subject and a body part of the subject; and, a wire wound around the support structure, wherein the wire is conductive, and wherein the wire is configured to be coupled electrically with the electrical leads of the field generator such that the electromagnetic field is generated at or near the support structure to provide therapy to the subject.

3. The system of claim 2, wherein the support structure comprises two intertwined helically wound runners arranged in at least two complete revolutions per runner, wherein the support structure is arranged in a toroidal shape comprising a centroid.

4. The system of claim 3, wherein the wire is spirally wound around a first runner of the two intertwined helically wound runners such that the wire is arranged in a helical shape comprising an axis that coincides with the first runner.

5. The system of claim 1, further comprising: an amplifier configured to amplify the electrical signal to produce an amplified electrical signal such that the amplified electrical signal induces the alternating current.

6. The system of claim 1, wherein the transducer comprises a stethoscope.

7. The system of claim 1, further comprising one or more sensors configured to generate output signals, wherein the generated output signals correspond to one or more of electroencephalography (EEG) signals, electrocardiography (EKG) signals, magneto-encephalography (MEG) signals, and acoustic cardiograph signals.

8. The system of claim 1, wherein the field generator comprises two intertwined helically wound runners arranged in at least two complete revolutions per runner, wherein the two intertwined helically wound runners comprise a first runner and a second runner, wherein the field generator further comprises a first set of twisted conductive wires spirally wound around the first runner in a helical shape comprising an axis that coincides with the first runner, and wherein the field generator further comprises a second set of twisted conductive wires spirally wound around the second runner in a helical shape comprising an axis that coincides with the second runner.

\* \* \* \* \*